United States Patent [19]

Scott

[11] Patent Number: 5,048,684
[45] Date of Patent: Sep. 17, 1991

[54] COMPACT SYRINGE AND CATHETER PACKAGE

[75] Inventor: David F. Scott, Sandy, Utah

[73] Assignee: Becton, Dickinson and Company, Franklin Lakes, N.J.

[21] Appl. No.: 473,558

[22] Filed: Feb. 1, 1990

[51] Int. Cl.⁵ .......................................... B65D 85/20
[52] U.S. Cl. .................... 206/364; 206/459; 206/471
[58] Field of Search .............. 206/363–366, 206/370, 438, 443, 459, 461–471, 820

[56] References Cited

U.S. PATENT DOCUMENTS

| | | | |
|---|---|---|---|
| 2,750,719 | 6/1956 | Wandelt | 206/365 |
| 3,074,540 | 1/1963 | Beich et al. | 206/469 |
| 3,325,000 | 6/1967 | Edwards | 206/464 |
| 3,435,944 | 4/1969 | Ishii | 206/461 |
| 3,759,375 | 9/1973 | Nappi | 206/362 |
| 4,075,639 | 1/1963 | Lingley | 206/366 |
| 4,324,331 | 4/1982 | Ignasiak | 206/461 |

FOREIGN PATENT DOCUMENTS

| | | | |
|---|---|---|---|
| 1361093 | 4/1964 | France | 206/363 |
| 1474882 | 3/1967 | France | 206/365 |
| 2334273 | 7/1977 | France | 206/461 |
| 0427154 | 6/1067 | Switzerland | 206/366 |

*Primary Examiner*—Jimmy G. Foster

[57] ABSTRACT

A package for a plurality of identical elongate articles each with a longitudinal axis and a head, center and tail. A pair of film members with abutting parts of their major surfaces are positioned along a common plane and pockets formed in the film members as nonabutting parts across from one another provide a plurality of article receiving spaces. Each article receiving space has a head, center and tail space to position an article with its head, center and tail in the respective spaces when the film members are attached to one another along the abutting parts. The article receiving spaces are disposed within the film members parallel in closely spaced and side by side relation for minimizing the abutting major surfaces between adjacent article receiving spaces and the spaces are in head to tail relation so the axes of the articles received therein are substantially parallel. The film members are thermoformed polymer joined along abutting surfaces. The attached pair of film members have a parting line defining at least one complete package separable from the next adjacent package having an article receiving space.

4 Claims, 4 Drawing Sheets

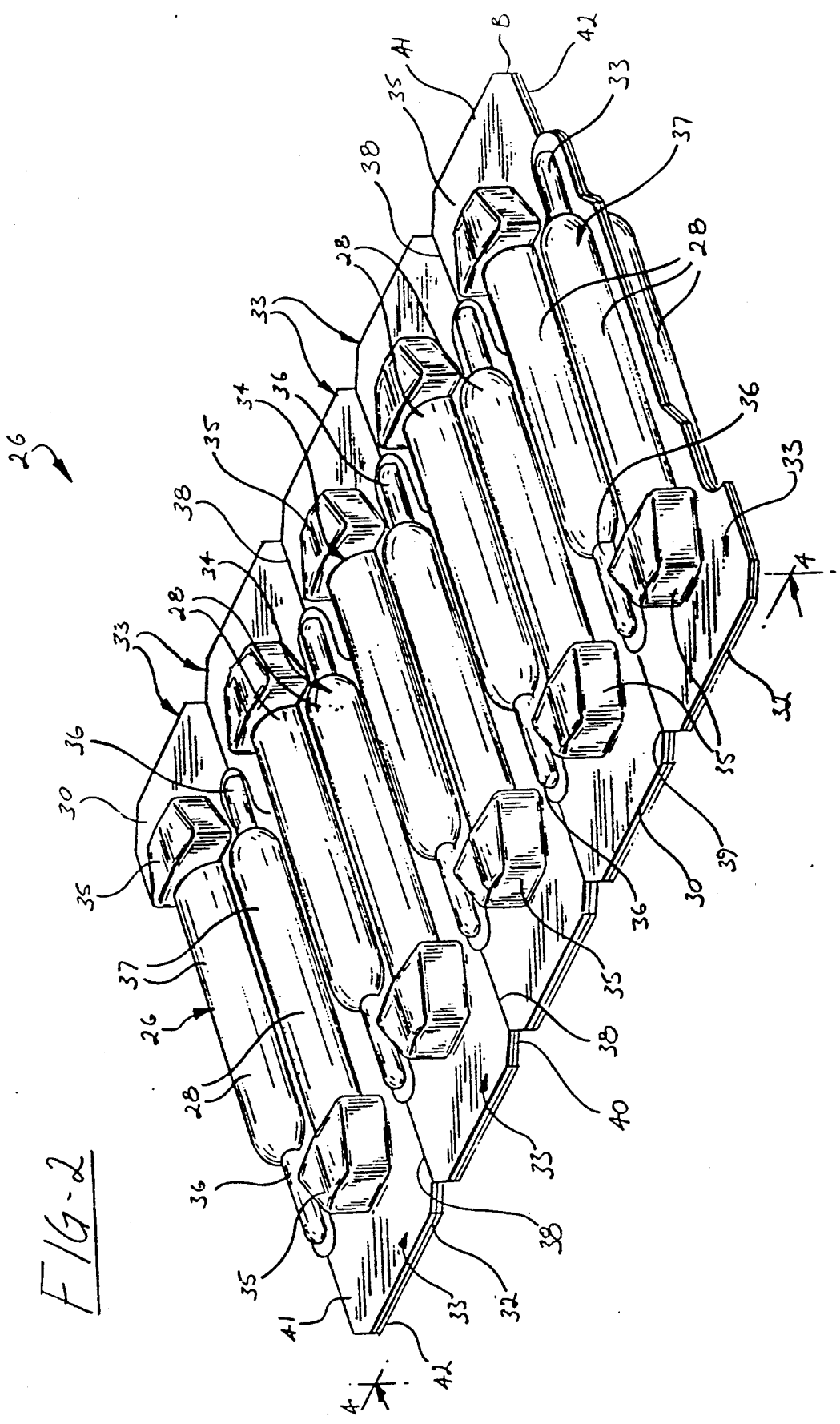

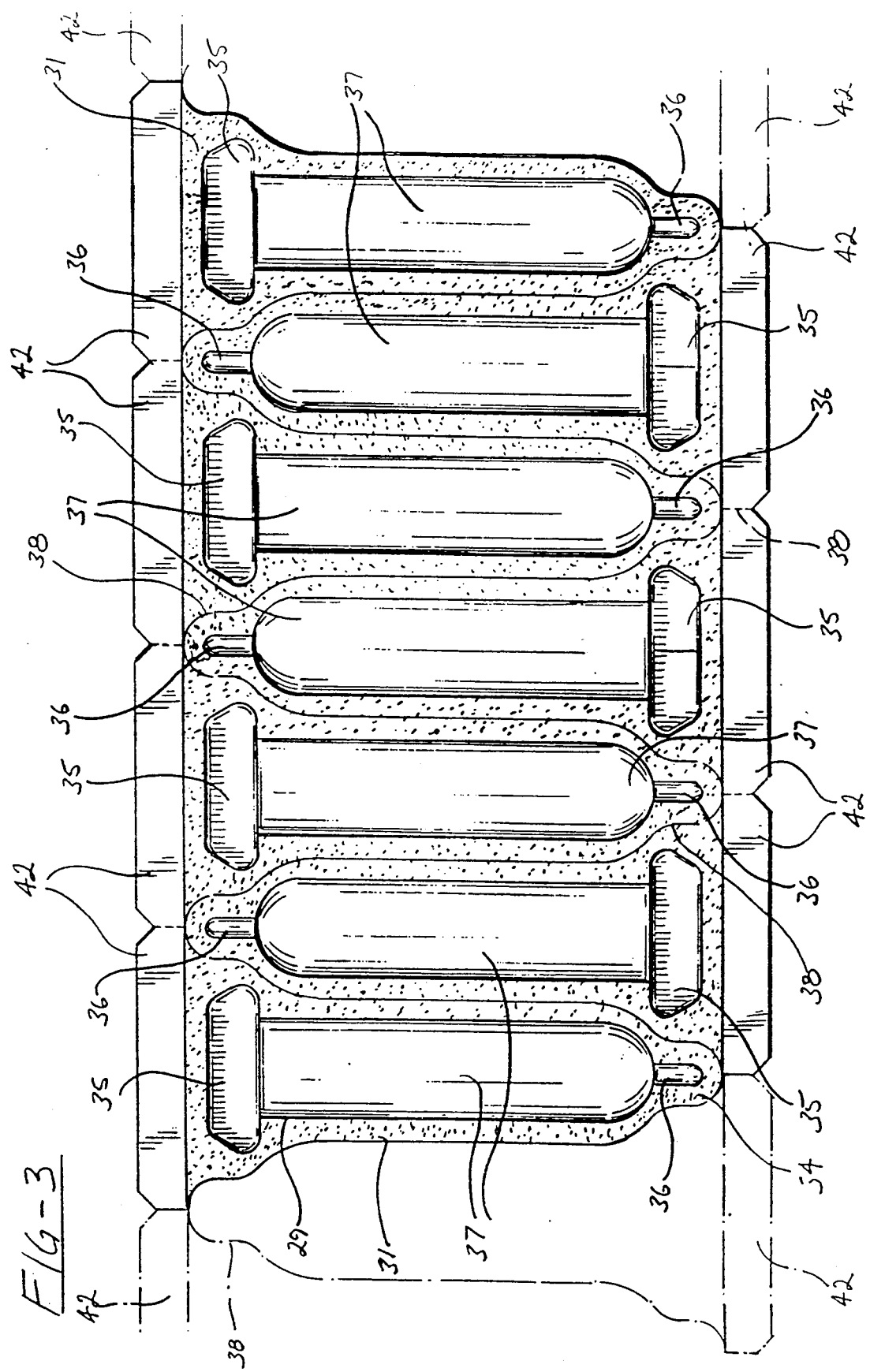

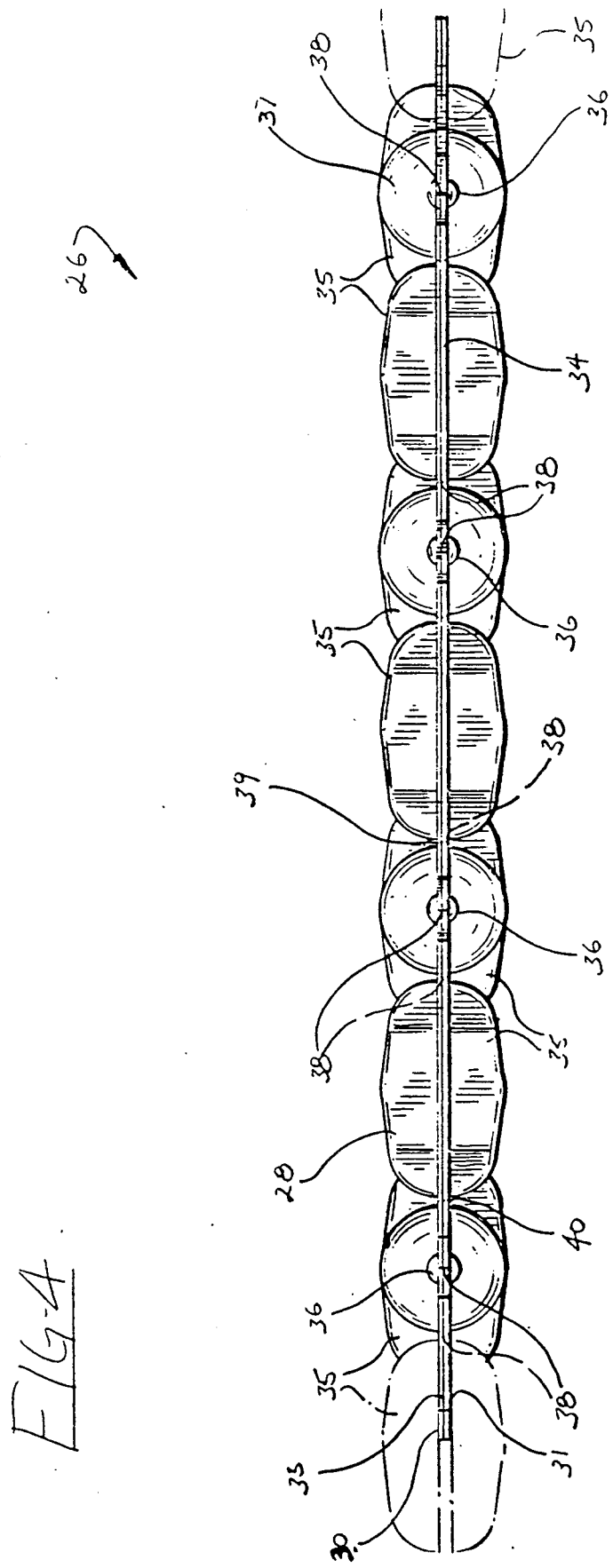

5,048,684

COMPACT SYRINGE AND CATHETER PACKAGE

BACKGROUND OF THE INVENTION

1. Field of the Invention

The invention relates to packaging for products such as disposable medical devices, and more particularly, concerns packaging for a plurality of identical disposable medical devices, such as syringes, catheters or the like.

2. Background of the Invention

Disposable medical devices are sold in groups of like size and type which are typically carried in an over carton in a dozen or more individually packaged, identical devices. A package can be removed from the over carton and opened to obtain a single disposable device. Individual packaging maintains a sterile barrier for each disposable medical device. Consequently, the package for each should be inexpensive, easy to open without contamination of the product and structurally adequate to protect the product prior to use.

Commonly used packaging for disposable medical devices include two components; a flat top or cover with printed product information as, for example, product size, type, name of manufacturer, instructions and the like. The top or cover is usually a thin sheet of extrusion coated paper having a polyethylene layer and a heat sealable lacquer layer. The paper is called Thillmany paper and the polyethylene is added for tear resistance.

The other or second component of the often used package is a drawn semi rigid tub which has a recess for receiving the product and a flange for supporting the top or cover. The tub is thermoformed from semi rigid polystyrene sheet which is heated and drawn such that the depth of the recess is no more than one and one-half times the width. Products which are wider than they are deep have to be packed sideways or the package has to be drawn less than required for efficient use of the drawn polystyrene material. Typically, the flange is the thickest part of the formed tub in that it is not drawn and the corners of the recess are the thinnest area because they are stretched the most. A ratio of flange thickness to corner thickness of six to one is about the maximum amount of thinning that can be accomplished with an economical starting thickness for the polystyrene sheet. The flange protects the device and provides support during opening.

The cover and tub flange are heat sealed to securely enclose the product within the recess of the tub but a portion along an edge is usually left unsealed in order to provide an area where the top can be peeled from the flange. In particular, the unsealed portion of edge of the top can be fanned away from the edge of the flange and then grasped and peeled away from the heat sealed areas about the rest of the flange. The product remaining within the recess is supported thereby during peeling. After removal of the top or cover, the product can be accessed without having violated the sterile field of the product but the use of gloved hands is necessary to maintain sterility. Since the product and package are typically sterilized after assembly but before use, the package has to remain a barrier to microbes and the like until the described opening procedure is performed.

There are disadvantages with the presently used packages including the amount of material, the time in processing the ease of use. The material problem is the original thickness of the styrene semi-rigid film needed to form an adequate recess for the product. A rather generic shape of recess is usually required to provide the space necessary to accommodate the product. Printing on the tub prior to forming will be distorted during forming unless complicated pre-distorted printing is used or difficult after forming printing is applied.

While less material and cheaper packaging films are available, such as, the use of a single wrap of material forming a tube with heat sealed ends, that approach will not adequately protect the product after assembly and will not support the product during opening. Consequently, the two component, tub and top package is commonly used for packing disposable medical devices.

An inexpensive preprinted package of a thin material is desired. The package has to open in a manner which will protect the sterile product and allow the parts of the package to be separated without loss of the sterile field or of the support of the product. The package should also protect the product after assembly and prior to package opening for use. That is to say that sufficient package rigidity is needed to prevent damage to the product during shipping and unwrapping. Disposable medical devices are usually made of molded polymeric materials and carry a hollow metal needle at one end. Medical products have light and accurately made parts designed to be handled gently when administering medication. Those medical products are such that the packaging is particularly important in preventing damage prior to use.

High volume production techniques and equipment used to manufacture disposable medical devices permit low unit cost and single use. Single use is important in preventing the spread of disease and infection. Consequently, any improvement which will lower the manufacture, assembly or shipping expense is of value in connection with maintaining the lowest possible unit cost and assuring a practical single use product. The package for a disposable medical device should have a minimum cost as the package has a shorter life than the device. In addition, minimizing the package lessens the amount of material which must be disposed of upon removal of the product. Disposable medical devices are packed in an over carton or shipper for carrying a group of similarly sized products. The individual packaging of each device should facilitate the placement of a group into the over carton and allow easy removal of a single packed device.

U.S. Pat. No. 4,444,310 discloses a segmented multi-product package containing articles such as hypodermic syringe tip caps. There is a tray which contains a plurality of receptacles having open ends associated with an upper surface of the tray. A sealing area around the upper surface lies between adjacent open ends and the cover is removably sealed across these areas to cover the receptacles and enclose the syringe tip caps. This is a typical package for disposable medical products as described.

U.S. Pat. No. 4,438,845 discloses a package for a syringe having top and bottom chambers with a platform therebetween and an elongate opening in the platform provides an entrance opening into the bottom chamber such that syringes when discarded are deposited in the bottom chamber. This package represents essentially two of the common flat top packages herein before described placed against one another.

U.S. Pat. No. 4,015,709 includes a container in the form of an elongate tray for carrying a plurality of syringes with a removable label or cover heat sealed over the open top of the tray. The bottom wall of the tray includes notches for holding and positioning the syringes. This reference has a plurality of syringes carried in a common package using the conventional tray with a flat cover. U.S. Pat. No. 3,305,084 has a package similar to that shown in the '709 patent but the container top is formed and not flat. Again, the syringes are carried as a plurality of products separated in a tray with a notched bottom surface. Individual syringes can not be accessed without disturbing the sterility of others.

U.S. Pat. No. 4,699,291 teaches a package with first and second housing portions, each with a generic shaped recess and a flanged periphery. When the flanges are positioned adjacent to and engaged with one another, an article compartment is defined. The flanges are secured with a removable tube, slit longitudinally and positioned for causing positive engagement of the flanges to one another to maintain the housings together. Dimples may be included along the flanges in order to retain the tubing in position.

U.S. Pat. No. 3,454,210 has a package with a top and base member each having a preformed pocket, preselected areas about the pocket are bonded together to hold the package closed. The pockets are of a rather generic shape and there is no specific disclosure of the present semi rigid and formed package for individually securing disposable medical devices.

SUMMARY OF THE INVENTION

A package for a plurality of identical elongate articles each having a longitudinal axis and each with a head at one end and a tail at the other with a center therebetween wherein the package has a pair of film members with abutting parts of their major surfaces positioned along a common plane. There are pockets formed in the film members defining nonabutting portions thereof positioned across from one another to define a plurality of article receiving spaces within said film members generally centered about the common plane. Each article receiving space has a head space and a tail space with a center space therebetween for aligning the axis of each article substantially within the common plane and for positioning an article within each article receiving space with its head, center and tail in the respective spaces of each pocket when the film members are attached to one another along the abutting parts.

The pockets may have the article receiving spaces being disposed within the film members in parallel relation relative to one another so the axes of the articles received therein are substantially parallel to one another. The article receiving spaces are preferably located in the film members in closely spaced side by side relation adjacent to one another for minimizing the abutting major surfaces between adjacent article receiving spaces. The closely spaced side by side adjacent article receiving spaces defined by the pockets are most preferably set in head to tail relation relative to one another so the head space for one article is positioned near the tail space of at least one adjacent article.

The article receiving spaces formed across from one another in the pair of abutting film members may be mirror images of each other and a part of the abutting film members along edges thereof generally normal to the axis of the article might be unattached for use in separating the abutting film members.

The pair of film members are in the preferred package made of a polymeric material and the pockets are formed in the polymeric material by heating and then stretching under pressure. The pair of film members may be substantially transparent thermoformed polyolefinic polymer. The pair of film members are preferably preprinted prior to thermoforming with regular indicia which is not substantially distorted by thermoforming. The film members are in the preferred package attached to one another at the abutting major surfaces by melting and pressure applied to join the melted surfaces.

The film members may also be in another embodiment attached by adhesive along at least parts of the abutting major surfaces. The attached pair of film members could include a parting line defining at least one complete package having an article receiving space separable from the next adjacent package having an article receiving space.

BRIEF DESCRIPTION OF THE DRAWINGS

FIG. 2 is a top perspective view of a different package for a plurality of identical articles such as syringes and the bottom film member is formed identical to the top and the bottom which are designed for holding each article apart from another in head to tail relation.

FIG. 3 is a plan view of one half of the package for a plurality of identical articles of FIG. 2 with the top half removed and showing the surface which abuts, and the nonabutting surface providing the article receiving space.

FIG. 4 is a side elevational view of the package for the plurality of identical article of FIG. 2 as taken along line 4—4 of FIG..2 and showing the relationship between the top and bottom of the package which include pockets and abutting portions proximate to each other.

DETAILED DESCRIPTION OF THE DRAWINGS

Figure 1:
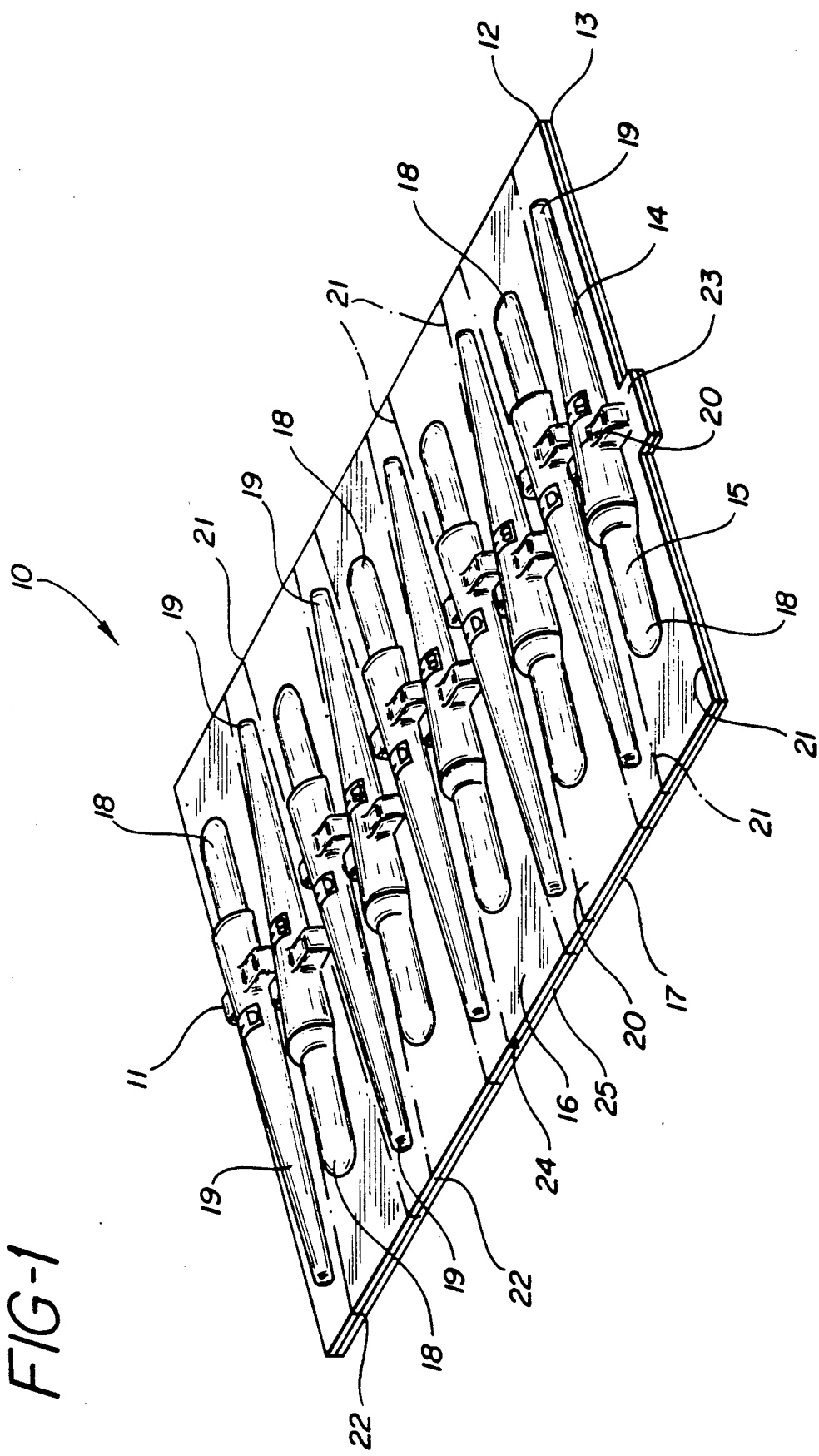
FIG. 1 is a top perspective view of a package for a plurality of identical articles such as catheters illustrating the thermoformed pockets which receive the articles and the relative spacing and positioning of each.

While this invention is satisfied by embodiments in many different forms, there is shown in the drawings and will herein be described in detail, a preferred embodiment of the invention and an alternative embodiment, with the understanding that the present disclosure is to be considered as exemplary of the principles of the invention and is not intended to limit the invention to the embodiments illustrated. The scope of the invention will be measured by the appended claims and their equivalents.

The compact package 10 shown in FIG. 1 is a top perspective view for a plurality of identical articles, such as catheters, held within pockets 11 resulting from thermoforming of a pair of flat sheets (not shown) of polymeric material. The package 10 preferably formed of an olefinic material sheet which can include a transparent top film I 2 and an opaque bottom film 13 to effectively display the product. The top sheet 12 can be preprinted with regular indicia (not shown); the thermoforming is so slight for one half the package 10 that it does no distort the printing. In FIG. 1 there is an outline 14 of the shape of a catheter which outline 14 defines an article receiving space 15 and that is one half of a pocket 11. The outline 14 of the catheter is formed in the top film 12 and the bottom film 13 such that there remain abutting major surfaces 16 and 17 respectively for top film 12 and bottom film 13. Under heat and pressure the top film 12 and bottom film 13 are thermoformed to create the pockets 11.

In particular, the article receiving space 15 is defined by the placement of the thermoformed parts of pockets 11 across from one another and in one preferred form wherein the top film 12 and the bottom film 13 are the same a mirror image relation results. The shape of the catheter outline 14 of each pocket 11 includes a head space 18, a tail space 19, and a center space 20 therebetween which are shaped to hold an individual catheter. While the pockets 11 are identical mirror images of each other and a plane A defined by the abutting surfaces 16 and 17 is centered, this is not a requirement since the pockets can be of different shapes to hold a non-symmetrical product.

The top film 12 and the bottom film 13 each include parting lines 21 and 22 respectively. The parting lines surround each individual compact package 10. The parting lines 21 and 22 define an area of weakness extending through part of the thickness of films 12 or 13 respectively, thus permitting an individual compact package 10 to be removed from the plurality of packages shown in FIG. 1.

The parting lines 21 and 22 follow the outline 14 of the product packaged e.g. in FIG. 1 the edge 23 formed by detaching a package 10 has the shape of the cut formed by the parting lines 20 and 21. For economical use of material, adjacent packages 10 are conjugate as much as possible to minimize the amount of film material necessary for the top film 12 and the bottom film 13.

On each package there is a side edge 24 on top film 12 and a side edge 25 on bottom film 13 located along a portion of the individual package 10 near either the head space 18 or the tail space 19. These side edges 24 and 25 are designed for ease in opening a package 10. In particular, the edges 24 and 25 may be fanned apart from one another such that they can be grasped between the forefingers and thumbs of the hands of the user for peeling apart to open the package 10 by separating the top film 12 from the bottom film 13. The major abutting surfaces 16 and 17 can be attached to one another by either heat sealing, welding or adhesives over most of their area but ar not attached near the side edges 24 and 25 for top film 12 and 13 respectively whereby the films can be peeled from one another.

FIG. 2 shows a package 26 similar to package 10 but designed for holding a syringe instead of the catheter. Therefore, the outline 27 for the syringe is shaped differently than the outline 14 for the catheter. It will be noted however that the positioning of the respective article receiving pockets 15 of FIG. 1 and 28 of FIG. 2 are in general in head to tail parallel spaced relation whereby the economical use of material is obtained. The outlines 27 define conjugating shapes of head to tail parallel syringes provides for efficient material use.

In FIGS. 2 and 3 the top film is 30 and the bottom film is 31 and the respective pockets 28 formed are defined by major abutting surfaces 33 and 34 of the top film 30 and bottom film 31. There is a head space 35 which holds the thumb pressing end of the plunger for a syringe and there is a tail space 36 which holds the needle receiving end of the syringe and the center space 37 which holds the barrel of the syringe. These various spaces are the shape of the pocket 28, half of which is thermoformed in the top film 30 and a similar mirror image pocket half is thermoformed in the bottom film 31. While the pockets 28 are identical mirror images of each other and the plane B defined by the abutting surfaces 33 and 34 is centered, this is not a requirement since the pockets 28 can be of different shapes to hold a non symmetrical product. The positioning of the respective pockets 28 is such that the head space 35, center space 37 and tail space 36 form the pocket 28 between the films 30 and 31 for a syringe which is held therein with its longitudinal axis along the plane B on which the abutting surfaces 33 and 34 of the films 30 and 31 meet.

The individual packages 26 for each syringe are defined by parting lines 38 positioned between the respective packages 26 whereby a single package 26 can be removed from the plurality of packages 26 shown in FIG. 2. The parting line 38 includes a partially cut line 39 in top film 30 and 40 in bottom film 31 and defining an area of weakness along which a package 28 for a syringe may be separated. The major abutting surfaces 33 and 34 can be attached to one another by either heat sealing, welding or adhesives over most of their area but are not attached along side edges 41 and 42 for top film 30 and bottom film 31, respectively whereby the films 30 and 31 can be peeled from one another. To facilitate the removal of the syringe from the package, the side edges 41 and 42 can be fanned apart and peeled away one from the other.

FIG. 3 shows a top plan view of the bottom film 31 of FIG. 2. The top film 30 is removed and the major abutting surface 34 is shown stippled for indicating its location. There are a series of about one half of each thermoformed pocket 28 for receiving a disposable medical device such as a syringe. The syringe receiving space formed by the portion of the pocket 28 is of a depth sufficient to contain about one-half of a syringe. The other half would be contained in a similar preformed top film 30 which, as explained, would be disposed over the bottom film 31 such that the complete pockets 28 are formed when top and bottom films 30 and 31 are aligned to form a mirror image of one another and are join at abutting surfaces 33 and 34. The individual pockets 28 are arranged in side by side, head to tail parallel spaced relationship wherein the axis of the respective syringes will be generally parallel to each other and along the common plane B defined by the abutting surfaces 33 and 34.

The parting line 38 defines the individual packages 26 and circumscribes each individual package 26. The unsealed side edge 42 is shown in FIG. 3 and a similar edge 41, as explained, in connection with FIG. 2, would rest atop side edge 42 whereby the side edges of the top film 30 and the bottom film 31 can be fanned apart in order that the top may be peeled from the bottom.

FIG. 4 is a side elevational view of the packages 26, shown in FIG. 2, as if viewed along line 4—4 of FIG. 2. The reference numbering in FIG. 4 is identical to that of in FIGS. 2 and 3 and the end view of FIG. 4 shows more clearly the parting line 38 as it extends about the individual packages 26. Most preferably, the parting line 38 is pierced into the top film 31 at 40 and bottom film 31 at 38 as the films are heat sealed together.

The polymer material used to thermoform package 10 or 26 should be acceptable for purposes of sterilizing. One preferred method of sterilization is Gamma radiation and certain polymers have been found to resist deterioration when irradiated sufficiently to sterilize the package 10 or 26 and the product contained therein. After manufactured products are placed in a thermoformed bottom, a thermoformed top is aligned there-over so that either pockets 11 or 28 result when the films are joined at the abutting surfaces.

The amount of thermoforming of the package is most preferably limited such that preprinted film will not loose its regularity or become illegible. It also should be understood that the abutting surfaces 16 and 17 or 33 and 34, although minimized, form a support to lend substance to the individual packages 10 or 26 which resists deformation of the individual pockets 11 or 28 and protects the article in the package.

Particular packaging has been shown and described in connection with catheters and syringes, but the claims which follow cover any kind of article packaged in accordance with the concept of the placement of the product, approximately between two thermoformed films wherein the thermoforming is relatively shallow but sufficient to contain about half of the product. While not specifically shown in any of the views, the idea of preprinting the film prior to forming is a part of the invention as well as using a variety of different film materials and attaching the films to one another by heat sealing, welding, adhesives or any other similar means. The preferred embodiment is a thermoformed polyolefinic film, which is formed under heat and pressure; cold forming techniques with other materials can be used without departing from the claimed invention.

What is claimed is:

1. A package for a plurality of identical elongate articles each having a longitudinal axis and each with a head at one end and a tail at the other with a center therebetween wherein the package comprises;
   a) a pair of film members which have preprinting over at least the area of the pockets prior to thermoforming with regular indicia which is not substantially distorted by thermoforming with abutting parts of their major surfaces positioned and attached to each other along a common plane;
   b) pockets formed in the film members defining non-abutting portions thereof positioned across from one another to define a plurality of article receiving spaces each shaped with the outline of the article to be packaged within said film members generally centered about the common plane, each article receiving space having a head space and a tail space with a center space therebetween for aligning the axis of each article substantially within the common plain and for positioning an article within each article receiving space with its head, center and tail in the respective spaces of each pocket when the film members are attached to one another along the abutting parts and the article receiving spaces are located in the film members in closely spaced conjugate side by side relation adjacent to one another for minimizing the abutting major surfaces between adjacent outlines and the closely spaced side by side adjacent article receiving spaces defined by the pockets are set in head to tail relation relative to one another so the head space for one article is positioned near the tail space of at lease one adjacent article.

2. The package for the plurality of identicle articles of claim 1 wherein the pair of film members are made up of polymeric material.

3. The package for the plurality of identical articles of claim 2 wherein the pair of film members are substantially transparent thermoformed polyolefinic polymer.

4. The package of the plurality of identical articles of claim 1 wherein the attached pair of film members include a parting line defining at least one complete package having an article receiving space separable from the next adjacent package having an article receiving space.

* * * * *